United States Patent [19]

Simmons et al.

[11] Patent Number: 5,895,651
[45] Date of Patent: Apr. 20, 1999

[54] RECOMBINANT DENGUE VIRUS ENVELOPE PROTEIN/MALTOSE-BINDING PROTEIN ANTIGENS AND SUBUNIT VACCINE COMPOSITIONS CONTAINING SAID ANTIGENS

[75] Inventors: Monika Simmons, Gaithersburg; Curtis G. Hayes, Frederick; Kevin R. Porter, Gaithersburg, all of Md.

[73] Assignee: The United States of America as represented by the Secretary of the Navy, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/671,056

[22] Filed: Jun. 27, 1996

[51] Int. Cl.$^6$ .......................... A61K 39/00; A61K 39/12
[52] U.S. Cl. .................... 424/192.1; 424/218.1; 424/185.1; 530/350
[58] Field of Search .................. 435/69.1, 172.3; 424/185.1, 186.1, 201.1, 192.1, 218.1

[56] References Cited

U.S. PATENT DOCUMENTS 5,494,671  2/1996  Lai et al. ..................... 424/218.1

OTHER PUBLICATIONS

Mason et al., 1990, J. Gen. Virol. 71:2107–2114.
Makino et al., 1991, Am. J. Trop. Med. Hyg. 45:636–643.
Megret et al., 1992, Virol. 187:480–491.
Stanley et al., 1995, Vaccine 13:947–951.
Stephenson, J., 1988, Vaccine 6:471–480.
Kurane et al., 1992, Sem. Immunol. 4:121–127.
Smucny et al., 1995, Am. J. Trop. Med. Hyg. 53:432–437.
Morens et al., 1990, J. Gen. Virol. 71:2909–2914.

*Primary Examiner*—Donald E. Adams
*Assistant Examiner*—Jeffrey S. Parkin
*Attorney, Agent, or Firm*—A. D. Spevack, Esq.

[57] ABSTRACT

A recombinant fusion protein (DEN-2 MBP) containing the B domain of the dengue (DEN 2 envelope protein is disclosed as a candidate subunit immunogen for vaccination against dengue virus infection. A gene fragment encoding amino acid 298 to amino acid 400 of the DEN-2 virus envelope was expressed as a fusion protein with the maltose binding protein (MBP) of *Escherichia coli* (*E. coli*). The recombinant fusion protein was purified and analyzed for its antigenicity imunogenicity and ability to protect mice against lethal challenge. This antigen is detected by monoclonal antibody (3H5) which is specific for a neutralizing epitope on the DEN-2 envelope and reacted with homologous polyclonal mouse immune ascitic fluid and DEN-2 immune human sera. A recombinant fusion plasmid bearing the DEN-2 MBP DNA sequence, expressing the fusion product in *E. coli* is disclosed. The fusion protein when administered to a host elicits a virus neutralizing antibody response which confers partial protection to the recipient animals against challenge infection. Sera from immunized mice revealed no neutralizing antibodies to any of the other DEN serotypes in the plaque reduction neutralization assay (PRNT).

14 Claims, 1 Drawing Sheet

MALTOSE BINDING PROTEIN (MBP)     DENGUE ENVELOPE FRAGMENT

| MALTOSE BINDING PROTEIN (MBP) | DENGUE ENVELOPE FRAGMENT |

FIG. 1

RECOMBINANT DENGUE VIRUS ENVELOPE PROTEIN/MALTOSE-BINDING PROTEIN ANTIGENS AND SUBUNIT VACCINE COMPOSITIONS CONTAINING SAID ANTIGENS

BACKGROUND OF THE INVENTION

1. Field of the Invention

This invention relates to an immunologically active fusion protein, useful in vaccination against dengue (DEN) virus as well as a diagnostic antigen. More particularly, this invention relates to a fusion protein antigen containing 366 amino acids of a maltose binding protein (MBP) from E. coli fused to 103 amino acids of the DEN envelope protein. This fusion protein antigen reacts with mouse monoclonal (3H5) and polyclonal (HIAF) antibody to dengue virus as well as human anti-DEN antibody, making it a useful antigen for diagnostic assays and when administered as a vaccine, can confer protective immunity to a substantial proportion of vaccinated subjects.

2. Description of the Prior Art

Prevention of DEN infections would alleviate a major health problem in tropical and subtropical areas of the world. Each of the four DEN serotypes may cause dengue fever and the more severe illnesses, dengue hemorrhagic fever (DHF) and dengue shock syndrome (DSS). Infection with any one serotype of DEN appears to confer lifelong immunity to reinfection with the same serotype, but not to the other serotypes. Individuals sequentially infected with a different dengue serotype (secondary infection) appear to be at higher risk for developing more severe disease. Immmune enhancement has been proposed as the mechanism responsible for DHF/DSS. Because of this phenomenon, an effective vaccine must be either serotype specific or be against all four serotypes of dengue virus to insure that vaccination against a single serotype does not enhance infection with a different serotype.

Despite more than 50 years of effort, safe and effective vaccines have not been developed. Attempts to produce cell culture-derived live attenuated dengue vaccines by long term passage in primary kidney (PDK) cells were tried unsuccessfully (Ennis et al., J. Inf. Dis., 158:876–880, 1988). A dengue-1 candidate was shown to be genetically unstable (McKee et al., Am. J. Trop. Med. Hyg., 36(2):435–442, 1987). Other dengue 2, 3 and 4 candidates were also not suitable because they were either unstable, caused unmodified dengue fever or produced low levels of neutralizing antibody (Bancroft et al., J. Infect. Dis., 149:1005–1010, 1984, Hoke et al., Am. J. Trop. Med. Hyg., 43(2):219–226, 1990, Innis et al., Am. J. Trop. Med. Hyg., 40(6):676–687, 1989).

DEN viruses are composed of a single-stranded RNA molecule of positive polarity that is translated into three structural proteins, the capsid (C) protein, the membrane (M) protein, and the envelope (E) glycoprotein followed by seven nonstructural proteins (Henchal and Putnak, Clin. Microbiol. Rev., 3(4):376–396, 1990). The E protein is the major surface component of the virion membrane, it mediates virus binding to cell receptors and interacts with neutralizing antibody. Neutralizing antibodies are believed to correlate with protection (Henchal and Putnak, Clin. Microbiol. Rev., 3(4):376–396, 1990). Studies have shown that the E protein of DEN viruses contain cross reactive, subgroup specific, and serotype specific antigenic determinants and has been shown to elicit a protective immune response (Gentry et al., Am. J. Trop. Med. Hyg., 31:548–555, 1982, to Mc Cown et al., Am. J. Trop. Med. Hyg., 42(5):491–499, 1990). Immunization of rabbits with a purified native 33 kDa E protein fragment of the 17D Yellow Fever (17DYF) virus produced neutralizing antibodies and protection against intracerebral challenge (Brandriss et al., J. Enf. Dis., 161:1134–1139, 1990). Mice immunized with native purified DEN-2 envelope protein developed neutralizing antibodies and were protected against lethal virus challenge (Feighny et. al., Am. J. Trop. Med. Hyg., 47(4):405–412, 1992).

Several laboratories have reported production of recombinant DEN virus structural and nonstructural proteins in expression vectors including baculovirus, vaccinia virus and E. coli (Bray et. al., J. Virol., 63:2853–2856, 1989, Bray et al., J. Virol., 185:505–508, 1991, Lai et al, Vacc., 89:351–356, 1989, Mason et al., Virol., 158:361–372, 1987, Mason et al., J. Gen. Virol., 70:2037–2049, 1989, Men et al., J. Virol., 65:1400–1407, 1991, Putnak et al., Am. J. Trop. Med. Hyg.,45:159–167, 1991, Putnak et al., Virol., 163:93–103, 1988, Zhang et al., J. Virol. 62:3027–3031, 1988). Success with recombinant proteins as vaccines in the murine model has been variable. Some baculovirus recombinants have shown protection against virus challenge, but they were membrane-associated, making them difficult to purify without denaturation and were produced in low yields (Lai et al., Vacc., 89:351–356, 1989, Putnak et al., Virol., 163:93–103, 1988, Zhang et al., J. Virol., 62:3027–3031, 1988). As crude antigens they elicited low levels of neutralizing antibodies in mice, making them unlikely candidate vaccines. Vaccinia virus expressing the E protein and nonstructural protein one (NS1) used as a live recombinant virus failed to elicit a detectable seroresponse to either protein (Zhao et al., J. Virol., 62:4019–4022, 1987). An E. coli produced fusion protein with staphylococcal protein A containing 269 amino acids of the DEN-2 E protein and NS1 protein was recently reported to elicit neutralizing antibodies and protected mice against lethal challenge (Srivastava et al., Vacc., 13:1251–1258, 1995). Staphylococcal protein A however, has a high binding affinity for human immunoglobulin G, eliminating this fusion protein as a candidate vaccine (Kobatake et al., Anal. Biochem., 208(2):300–305, 1993). Recombinants containing the B domain of the E protein as a fusion protein with TrpE were expressed in E. coli as insoluble intracellular inclusion bodies and required detergents for its purification. These purified preparations did not elicit neutralizing antibodies in immunized mice nor did they confer protection against virus challenge (Fonseca et al., Am J. Trop. Med. Hyg., 44(5):500–508, 1991).

SUMMARY OF THE INVENTION

Accordingly, an object of this invention is recombinant fusion proteins containing a fragment of an envelope protein of a serotype-specific Dengue virus fused to a protein fragment having the amino acid sequence of a maltose binding protein from E. coli. (MBP).

Another object of this invention is recombinant subunit vaccines containing the fusion protein of MBP to the fragment of the corresponding region of the serotype-specific DEN envelope protein.

An additional object of the invention is the production of virus neutralizing antibodies produced in response to serotype-specific DEN-MBP fusion products for use in passive immunization as well as for other therapeutic purposes.

A further object of the invention is a plasmid containing the DNA sequence coding for the serotype-specific DEN-MBP fusion protein.

An additional object of this invention is the use of serotype-specific DEN-MBP fusion proteins as diagnostic antigens in immunoassays.

These and additional objects of the invention are accomplished by isolating a fragment of the serotype-specific Dengue virus envelope protein (DEN X E Protein) including at least amino acids 298–400. "X" is a number selected from 1, 2, 3, or 4 to denote a specific sero-type of the Dengue virus. The amino acid sequence of the fragment of interest of the DEN E protein for serotype 2 and 4 is the same (298–400), for DEN 1 it is amino acid 293-412, and for DEN 3 it is amino acid 297–398.

Using standard techniques, the DEN E protein fragment is inserted into a plasmid containing the nucleotide sequence coding for the amino acids of the Maltose binding protein of E. Coli. The plasmid is inserted into E. coli. and the fusion protein of the Dengue "X" virus fragment and Maltose binding protein (fusion protein) are expressed.

The fusion protein can be used as a type-specific diagnostic antigen in any of the accepted diagnostic tests. The fusion protein is maintained and used in the diagnostic solutions usually used to preserve a diagnostic protein such as glycerol etc. Further, the fusion protein of this invention can be injected into a host to produce type-specific virus neutralizing antibodies. These virus neutralizing antibodies can be isolated and reproduced through standard techniques and the virus neutralizing antibodies can be used as type-specific passive immunogens against Dengue fever.

In the embodiment of Dengue 2 illustrated in the specific examples, the fusion protein is formed of the fragment containing amino acids 298 to amino acid 400 of DEN 2 E protein fused to 366 amino acids of a maltose binding protein from E. coli. This protein is designated DEN 2 maltose binding protein (DEN-2 MBP). By DEN-2MBP we refer to a DEN virus serotype 2 specific maltose binding protein fusion.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements. The representations in each of the figures is diagrammatic and no attempt is made to indicate actual scales or precise ratios. Proportional relationships are shown as approximations.

FIG. 1 is a schematic diagram of the predicted general features of the amino acid sequence of DEN-2 MBP.

DESCRIPTION OF THE PREFERRED EMBODIMENTS

One of the problems with Dengue fever is enhancement of susceptibility to death caused by a reinfection of a subject. To avoid antibody-dependent enhancement of DEN virus, a suitable DEN vaccine should induce long-lasting type-specific antibodies. This is accomplished with a subunit vaccine containing proteins representing DEN type-specific protective antigens or combinations of type-specific antigens, but containing few or no DEN group-reactive epitopes. The illustrated embodiment of the invention is a construct containing 366 amino acids of the MBP of E. coli fused to 103 amino acids of the B domain of the DEN 2 E protein. Fonseca et. al described this region as disulfide-bridge dependent, indicating the importance of conformation and Trirawatanapong et. al showed that a 12 amino acid epitope of the DEN envelope protein located in this region was associated with the production of neutralizing antibody (Trirawatanapong et al., GENE, 116:139–150, 1992). Reactivity of the illustrated DEN-2 MBP fusion protein of this invention with hyper immune ascitic fluid, human sera and DEN-2 specific monoclonal antibody by Western blot and ELISA shows proper folding of the DEN-2 MBP fusion protein, as well as confirming the presence of the type-specific neutralizing epitope described by Trirawatanapong. Plaque reduction neutralization assays (PRNT) using sera from mice immunized with the DEN-2 MBP fusion protein revealed no neutralizing antibodies to any of the other serotypes, indicating the achievement of type-specificity required for a successful DEN subunit vaccine.

The maltose binding protein used as the carrier protein is involved in the translocation of maltose across the cytoplasmic membrane of E. coli (Duplay et al., J. Biol. Chem., 259(16):10606–10613, 1984). A sequence homology search was performed at the NCBI using the BLAST network service and revealed no sequence similarity with any known eukaryotic proteins. Therefore antibodies produced against MBP would not present a significant risk factor to human health. The enhanced immunogenicity observed with the DEN-2 MBP fusion protein is believed due to its ability to be expressed in a soluble form, resulting in proper folding, as well as providing a protective environment enhancing its stability. Another possible role for the MBP component might be the presence of T-helper cell epitopes aiding B-cells in antibody synthesis.

In contrast to the TrpE fusion protein discussed above, this invention is the fusion protein of a maltose binding fusion protein (MBP) and the B domain of the appropriate DEN E protein, expressed as a soluble protein. This fusion protein is easily purified by affinity chromatography. Mice immunized with the E. coli produced DEN-2 MBP fusion protein developed the highest reported neutralizing antibody titers for recombinant DEN subunit imunuogens and conferred significant protection against lethal virus challenge.

The recombinant fusion protein antigen DEN-2 MBP containing 103 amino acids of DEN virus E protein is a candidate immunogen for vaccination against DEN virus infections. The DEN-2 MBP antigen is detected by the monoclonal antibody (3H5) which is specific for a neutralizing epitope (Trirawatanapong et al., Gene, 116:139–150, 1992) on the DEN envelope. In addition, the DEN-2 MBP is detected by DEN specific antibodies in HIAFs and human sera when used in immunoassays such as the enzyme linked immunosorbent assay (ELISA), dot immunoassay (DOTIA) and Western blot. A recombinant prokaryotic expression plasmid bearing the DEN-2 MBP DNA sequence expresses the fusion protein in E. coli and introduction of this fusion protein antigen into mice elicits a type-specific virus neutralizing antibody response and confers significant protection to the recipient animals against challenge infection.

Having described the invention, the following examples are given to illustrate specific applications of the invention including the best mode now known to perform the invention. These specific examples are not intended to limit the scope of the invention described in this application.

EXAMPLE 1

Construction of the Fusion Plasmid

Cloning.Plasmids containing viral cDNA were used as a source of template DNA in the polymerase chain reaction (PCR) to amplify the gene sequence coding for amino acid 298 to 400 of the DEN 2 envelope (Fonseca et al., Am. J. Trop. Med. Hyg., 44(5):500–508, 1991). Primers flanking this region were designed to include restriction sites present in the MBP expression vector pMALc (New England Biolabs, Beverly, Mass.). The purified PCR product was cloned into the pMALc vector and subsequently introduced into TB1 E. coli by standard techniques. Positive colonies were identified on agar plates by the white and blue selection method, and screened for the presence of inserts by restriction digest.

EXAMPLE 2
Charaterization of DEN-2 MBP

Western blotting and sequence analysis. Clones positive by restriction digest were grown in small cultures and expression was induced with isopropylthiogalactosidase (IPTG). DEN specific fusion protein was detected by Western blot using monoclonal and polyclonal ascitic fluids. Western blotting showed that the DEN-2 MBP reacts with DEN-2 specific monoclonal antibody (3H5), polyclonal antibody (HIAF) and DEN immune human sera. Western blotting also indicated that protein to have a molecular weight of 53 kD, comprised of the expected 42.7 kD of the MBP and 10 kD of the DEN envelope fragment.

The nucleotide sequence at the junction region between inserted cDNA and the maltose binding protein gene of the recombinant plasmid was examined for its reading frame by the dideoxy chain-termination method (Sanger et al., Proc. Natl. Acad. Sci., 74:5463–5467, 1977).

EXAMPLE 3
Purification of DEN-2 MBP recombinant fusion protein

One liter cultures were induced with IPTG and harvested after 4 hours of growth. The pellets were sonicated and affinity column purified per manufacturers instructions (NEB). Further purification was accomplished by SDS-PAGE using non-reducing sample buffer, where the fusion protein band was excised, electroeluted and dialyzed against PBS.

EXAMPLE 4
Antibody response against DEN-2 MBP is protective

Immunogenicity of the recombinant fusion protein was evaluated in 10 BALB/C mice immunized with the purified fusion protein. All mice developed antibodies reactive with DEN-2 virus infected cell lysate antigen in the ELISA. Neutralizing antibodies elicited by the DEN-2 MBP fusion protein measured by PRNT indicated higher anti-DEN-2 virus neutralizing antibody titers than any other reported recombinant DEN subunit immunogen. Furthermore, the neutralizing antibodies produced by our recombinant immunogen failed to neutralize any other DEN virus serotypes in the PRNT, indicating their type specificity. The immune response to the recombinant fusion protein was further evaluated in a protection experiment with 3-week-old BALB/c mice. Two groups of 9 mice were injected subcutaneously 3 times at 2 week intervals with 50 ug of DEN-2 MBP or MBP alone. One week after the last dose, the mice were challenged by i.c. injection of live DEN-2 virus (100 $LD_{50}$) and observed for 20 days. Brain suspensions of 4 mice in each group were prepared on day 6 after challenge. Plaque assays of mouse brain indicated virus titers of $10^2$ to $10^3$ PFU/ml in mice immunized with MBP alone and no plaques were detected in the DEN-2 MBP immunized group at a 1:10 dilution. Four of the remaining 5 DEN-2 MBP immunized mice survived i.c. challenge, whereas all mice immunized with MBP alone were dead by day 9 post challenge.

EXAMPLE 5
Use of DEN-2 MBP protein for vaccination of humans

Results indicate that the fusion of a type-specific antigenic determinant to the maltose binding protein of *E. coli* resulted in enhanced immunogenicity. Since a sequence homology search detected no known eukaryotic homolog to the MBP carrier protein, it is unlikely to have any adverse effects in humans. Recombinant proteins expressed by bacterial plasmids are administered to humans in any pharmacologically appropriate adjuvant including but not limited to saline, aluminum hydroxide, and liposomes.

EXAMPLE 6
Use of DEN-2 MBP fusion protein as a diagnostic antigen

Previous studies have shown that recombinant proteins engineered in *E. coli* as trpE fusion products with the B domain of the DEN envelope could be used as antigens in the ELISA (Fonseca et al. 1991. AM. J. Trop. Med. Hyg. 44(5):500–508). These antigens have shown to be DEN subgroup specific in the ELISA with HIAF and human sera. One problem encountered in using *E. coli* antigen preparations for serodiagnosis is the presence of antibodies in test sera that react with *E. coli* antigens. The trpE fusion products are produced as insoluble inclusion bodies and even after extensive purification exhibit non-specific reactivity. To overcome this problem, an additional absorption step is required in the ELISA. The DEN-2 MBP fusion product is produced in a soluble form allowing for the complete removal of contaminating *E. coli* proteins during purification, and therefore eliminating the absorption step.

EXAMPLE 7
Use of the murine model to study the immune response to DEN virus infections Humans, lower primates, and mosquitoes represent the only natural hosts of DEN virus infections. Several species of lower primates (chimpanzees, rhesus, gibbons and macaques) have shown to mount an immune response without any detectable clinical signs after infection (Halstead et al., J. Infect. Dis., 128:7–14, 1973, Whitehead et al., Am. J. Trop. Med. Hyg., 19:94–102, 1970, Rosen, Am. J. Trop. Med. Hyg., 7:406–410,1958, Scherer et al., Am. J. Trop. Med. Hyg., 27:590–599, 1978). The measurement of immune responses and protective efficacy requires a mammalian system and the mouse model represents the simplest system to use. Dengue viruses infect mice most effectively by the intracranial route and suckling mice usually die of encephalitis after 1 week (Kimura and Hotta, Nippon Igakku, 3379:629–633, 1944). Mice have been used extensively as models for studying the immune response to flavivirus infections and as subjects of test vaccines (Hotta, Warren H. Green, Inc., 36–44, 1969, Meiklejohn et al. Am. J. Trop. Med. Hyg., 1:51–58, 1952, Sabin and Schlesinger, Science, 101:640–642, 1945, Schlesinger et al., J. Gen. Virol., 68:853–857, 1987). The production of virus neutralizing antibodies and their ability to protect mice from lethal challenge, indicate that the mouse model is a useful tool in the development of a successful DEN vaccine.

Obviously, many modifications and variations of the present invention are possible in light of the above teachings. It is therefore to be understood that, within the scope of the appended claims, the invention may be practiced otherwise than as specifically described.

What is claimed is:

1. A fusion protein comprising a fragment selected exclusively from the B domain of the dengue X envelope protein and the maltose binding protein of *E. coli* wherein X is a number from 1–4.

2. The fusion protein of claim 1 wherein X is 1.
3. The fusion protein of claim 1 wherein X is 2.
4. The fusion protein of claim 1 wherein X is 3.
5. The fusion protein of claim 1 wherein X is 4.
6. The fusion protein of claim 2, wherein the dengue envelope protein consists of amino acid 293–412.
7. The fusion protein of claim 3, wherein the dengue envelope protein consists of amino acid 298–400.
8. The fusion protein of claim 4, wherein the dengue envelope protein consists of amino acid 297 to 398.
9. The fusion protein of claim 5, wherein the dengue envelope protein consists of amino acid 298 to 400.
10. The fusion protein of claim 7 wherein the maltose binding protein of E. coli contains 366 amino acids.
11. An immunogenic composition capable of inducing a neutralizing antibody response against dengue virus comprising the fusion product of a fragment selected exclusively from the B domain of the dengue X envelope protein and the maltose fusion binding protein of E. coli wherein X is a number from 1–4 in a pharmaceutically effective amount in an injectable solution.
12. The composition of claim 11, wherein X is 2 and the dengue envelope proteins consists of amino acids 298 to 400.
13. A plasmid consisting essentially of a nucleic acid fragment encoding a fusion protein comprising a fragment selected exclusively from the B domain of the dengue X envelope protein, wherein X is a number from 1–4 and the maltose binding protein of E. coli.
14. The plasmid of claim 13 wherein X is 2 and the nucleic acid fragment encodes amino acids 298 to 400 of the dengue envelope protein.

* * * * *